United States Patent [19]

van Eikeren et al.

[11] Patent Number: 5,677,469

[45] Date of Patent: Oct. 14, 1997

[54] PROCESS FOR RESOLVING CHIRAL ACIDS WITH 1-AMINOINDAN-2-OLS

[75] Inventors: Paul van Eikeren, Carlisle; Francis X. McConville, Grafton; Jorge L. López, Southborough, all of Mass.

[73] Assignee: Sepracor, Inc., Marlborough, Mass.

[21] Appl. No.: 446,255

[22] Filed: May 18, 1995

[51] Int. Cl.$^6$ ................................................. C07D 307/02
[52] U.S. Cl. ..................... 549/484; 562/401; 562/460; 562/466; 562/492; 562/493
[58] Field of Search ................ 549/484; 562/401, 562/460, 466, 492, 493

[56] References Cited

U.S. PATENT DOCUMENTS

| | | | |
|---|---|---|---|
| 4,246,164 | 1/1981 | Felder et al. | 260/501.17 |
| 5,015,764 | 5/1991 | Manimaran et al. | 562/401 |
| 5,162,576 | 11/1992 | Manimaran et al. | 562/401 |
| 5,191,112 | 3/1993 | Nohira et al. | 562/401 |
| 5,298,660 | 3/1994 | Yoneyoshi et al. | 564/302 |

FOREIGN PATENT DOCUMENTS

| | | |
|---|---|---|
| 0 482 797 | of 1992 | European Pat. Off. |
| 95/07880 | of 1995 | WIPO. |

OTHER PUBLICATIONS

Armstrong et al. "Stereocontrolled Addition of Chiral, Non--Racemic Amide Homoenolates to t-Boc-(S)-Phenylalaninal" *Tetrahedron Letters*, vol. 33, No. 44, 6599–6602 (1992).

Thompson et al. "Synthesis and Antiviral Activity of a Series of HIV-1 Protease . . . " *J. Med. Chem.* 35, 1685–1701 (1992).

Didier et al. "Chemo-Enzymatic Synthesis of 1,2– and 1,3– Amino–Alcohols and Their Use . . . " *Tetrahedron* 47, 4941–4958 (1991).

*Primary Examiner*—Amelia Owens
*Attorney, Agent, or Firm*—Heslin & Rothenberg, P.C.

[57] ABSTRACT

A process for the full or partial resolution of a mixture of enantiomers of a genus of chiral carboxylic acids is disclosed. The process uses a pure enantiomer of 1-aminoindan-2-ol as the resolving agent and achieves separation of the diastereomeric salts by fractional crystallization followed by liberation of the chiral acid from the salt by treatment with mineral acid. Diastereomeric salts and solvates of those salts are disclosed. The production of ketoprofen, flurbiprofen and other chiral medicaments and precursors thereto is disclosed.

24 Claims, No Drawings

5,677,469

PROCESS FOR RESOLVING CHIRAL ACIDS WITH 1-AMINOINDAN-2-OLS

FIELD OF THE INVENTION

The invention relates to the use of single enantiomers of 1-amino-2,3-dihydro-1H-inden-2-ol, hereinafter referred to as 1-aminoindan-2-ol

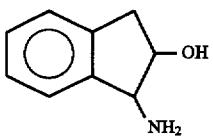

for resolving chiral acids.

BACKGROUND OF THE INVENTION

Several chiral amines are known for the resolution of chiral acids on a manufacturing scale. Notable examples include brucine, strychnine, quinine, quinidine, cinchonidine, cinchonine, yohimbine, morphine, dehydroabietylamine, ephedrine, deoxyephedrine, amphetamine, threo-2-amino-1-(p-nitrophenyl)-1,3-propanediol, α-methylbenzylamine, α-(1-naphthyl)ethylamine, and α-(2-naphthyl)ethylamine. Some of these chiral amines are expensive and are often difficult to recover. Furthermore, because many are natural products, usually only one enantiomer is readily available.

The use of some of the foregoing amines for the resolution of chiral 2-arylpropionic acids has been described. For example, U.S. Pat. No. 5,015,764 discloses using (S)-α-methylbenzylamine to resolve racemic ibuprofen. U.S. Pat. No. 5,162,576 discloses using (−)-cinchonidine to effect resolution of ketoprofen. These methods, however, have a number of limitations including the following: they are not general; they require considerable volumes of solvent; some require relatively high temperature; they produce product of less than optimal chemical and enantiomeric purity and accordingly require further purification steps; they are space-consuming and time-consuming; and they are difficult to carry out at commercial scale.

SUMMARY OF THE INVENTION

The object of the present invention is to provide a general, efficient, and cost-effective method to resolve organic acids that contain one or more chiral centers. A second object of the present invention is to provide a more time- and cost-efficient means to produce α-arylpropanoic acid antiinflammatory medicaments ("profens"), particularly (S)- and (R)-ketoprofen. The aminoalcohols according to the invention are substantially pure enantiomers of 1-aminoindan-2-ol.

Because 1-aminoindan-2-ol has two chiral centers, there exist two geometric isomers, each of which exists as a pair of enantiomers. Accordingly, there are four 1-aminoindan-2-ols pertinent to the present invention:

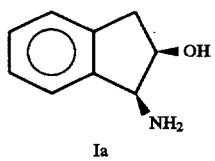 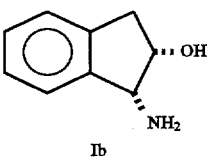

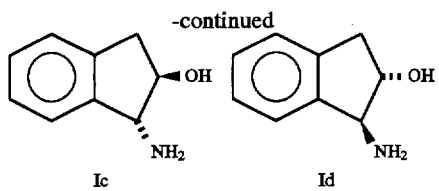

The aminoindanols of the present invention are simple and inexpensive to prepare, are readily resolved or obtained by asymmetric synthesis, are resistant to racemization under resolution conditions, and are readily recovered. The compounds of the present invention also have the advantage of being produced in the (+)- and (−) form with equal ease. This is in contrast to chiral resolving agents obtained from natural sources, which are generally available in only one form.

The invention relates to the use of a single enantiomer of aminoindanol, substantially free of other enantiomers of aminoindanol, for the resolution of a chiral acid. The chiral acid may be present in the form of a racemate or a mixture in which one enantiomer is in excess. The resolution can be accomplished by fractional crystallization.

One process for the resolution of a mixture of enantiomers of a chiral acid comprises the steps of;
(a) preparing a mixture of the chiral acid, or a salt thereof, with an enantiomer of 1-aminoindan-2-ol;
(b) separating the mixture into a first fraction enriched in one enantiomer of the acid as a diastereomeric salt and a second fraction enriched in the second enantiomer; and
(c) recovering the chiral acid from at least one of the fractions.

The chiral carboxylic acid is chosen from the genus of formula $$R^1R^2R^3CCOOH$$

wherein
$R^1$ is hydrogen or OH;
$R^2$ is methyl or cyclohexyl; and
$R^3$ is aryl, substituted aryl or heteroaryl;
or $R^2$ and $R^3$ together form a tetrahydrofuran or tetrahydropyran ring.

More particularly, the invention relates to a method for resolving a chiral carboxylic acid comprising the steps of:
(a) dissolving a mixture of enantiomers of a chiral carboxylic acid from the above genus in a suitable solvent;
(b) adding a substantially pure enantiomer of a 1-aminoindan-2-ol to create a diastereomeric salt of at least one enantiomer of the acid;
(c) allowing the diastereomeric salt to crystallize to form a solid phase, whereby the salt formed between 1-aminoindan-2-ol and a single enantiomer of the chiral acid predominates in the solid phase and the other enantiomer of the chiral acid, which may be as a salt or in part as the free acid depending on the amount of aminoindanol added, predominates in the solution phase;
(d) separating the solid phase from the solution phase; and
(e) recovering the chiral acid from at least one of the phases.

The 1-amino-2-indanol may be (1S,2R)-1-aminoindan-2-ol (Ia), (1R, 2S)-1-aminoindan-2-ol (Ib), (1R,2R)-1-aminoindan-2-ol (Ic), or (1S,2S)-1-aminoindan-2-ol (Id).

In various preferred embodiments of the chiral acid, $R^1$ is hydrogen and $R^2$ is methyl. Among such compounds, ketoprofen, ibuprofen, flurbiprofen, and naproxen may be noted. Ketoprofen is particularly preferred. Other preferred acids include those wherein $R^1$ is hydroxyl and $R^2$ is cyclohexyl. Tetrahydrofuran-2-carboxylic acid is also preferred. The enantiomer of 1-aminoindan-2-ol may be used in an amount of from 0.1 to 1.1 equivalents based on said carboxylic acid. For crystallization, 0.4 to 0.6 equivalents are preferred.

The foregoing process may further include the steps of recovering a non-racemic mixture of the enantiomers of the carboxylic acid, racemizing the mixture and recycling the racemized mixture. The non-racemic mixture will usually be enriched in the second enantiomer by virtue of the first enantiomer having been separated out as its diastereomeric salt.

In a composition aspect the invention relates to salts of an optically active 1-aminoindan-2-ol and a chiral carboxylic acid of the above formula. Preferred salts include those in which $R^1$ is hydrogen and $R^2$ is methyl, particularly salts of ketoprofen, ibuprofen, flurbiprofen, and naproxen. Salts of the profens, like ketoprofen, may be solvates with acetonitrile. Other preferred salts include those in which $R^1$ is hydroxyl and $R^2$ is cyclohexyl and those in which the chiral acid is tetrahydrofuran-2-carboxylic acid.

DETAILED DESCRIPTION OF THE INVENTION

The substantially enantiomerically pure aminoindanols needed for the process of the invention are, in the case of cis aminoindanols, synthesized by methods known in the art. [See for example Thompson et al. *J. Med. Chem.* 35, 1685–1701 (1992) and Didier et al. *Tetrahedron* 47, 4941–4958 (1991).] By substantially pure is meant that the ee is greater than 90%. In addition to the known methods, pure enantiomers of both cis and trans 1-aminoindan-2-ol may be prepared by the method disclosed in U.S. application Ser. No. 08/278,459, filed Jul. 21, 1994, the disclosure of which is incorporated herein by reference. The most pertinent part of that disclosure is reproduced here:

A 5-L three neck Morton-type flask equipped with an overhead stirrer, an addition funnel and a thermometer was charged with 2.5 L of NaOCl (10% aq, 2.0 eq, 4.0 mol). The solution was cooled to ca. 5°–10° C. A solution of (R,R)-Mn-Salen catalyst X

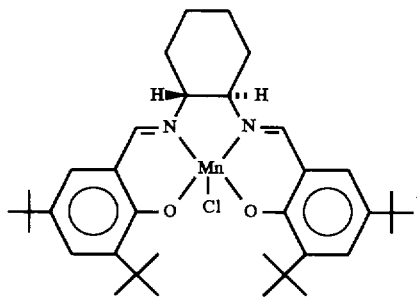

(19.1 g, 0.015 eq, 0.03 mol) in 150 mL of $CH_2Cl_2$ was added, followed by a solution of indene (260 mL, 1.0 eq, 2.0 mol) in 100 mL of $CH_2Cl_2$ at 5°–10° C. The mixture was stirred vigorously at 5°–10° C. for 4 hr. Heptane (1.4L) and Celite (40 g) were added and the mixture stirred for 40 min without cooling. The mixture was filtered and the flask and the solid cake were washed with 200 mL of heptane.

The combined filtrates containing partially resolved indene oxide were concentrated to ca. 400 mL and the concentrate treated with 1.4 L of aqueous ammonia (28% aq.) in 600 mL of MeOH in the presence of 20 g of Celite at 25°–30° C. for 15 hr. The MeOH and excess of ammonia were removed by distillation over a period of 4–5 hr until the pot temperature reached 90° C. Water (550 mL) was added and the hot mixture filtered. The flask and solid filter cake were washed with ca. 400 mL of hot water. The combined filtrates were placed under vacuum for 40 min to remove remaining ammonia and transferred to a 5-L Morton-type flask.

The above solution, containing partially resolved trans-(1S,2S)-1-aminoindan-2-ol, was cooled to ca. 15°–25° C. and NaOH (50% aq., 192 g) and acetone (800 mL) were added. Benzoyl chloride (1.2 eq, 2.4 mol, 280 mL) was added at 15°–25° C. over 1 hr and the resulting slurry stirred at 20°–25° C. for 2 hr. The mixture was filtered and the solid washed with 400 mL of acetone-water (1:1, v/v) and recovered as crude trans-benzamide of enantiomerically enriched trans-(1S,2S)-1-aminoindan-2-ol.

The crude benzamide (ca. 464 g) was dissolved in 1125 mL of DMF at 90° C. and MeOH (750 mL) was added at 80°–86° C. over 1 hour to the DMF solution. The solution was slowly cooled to 0°–5° C. over 1.5 h and held at 0°–5° C. for 2 h. The solid was recovered by filtration, washed with 500 mL cold (0°–5° C.) MeOH and dried under vacuum at 40° C. to give enantiomerically pure trans-benzamide of trans-(1S,2S)-1-aminoindan-2-ol as pale yellow crystals (240 g, 47% yield from indene, 99% ee, m.p. 232° C).

A mixture of the trans-benzamide (25 mmol, 6.33 g) from above and 58.3 mL of 6N aqueous HCl was refluxed for 14 hr, cooled to room temperature, washed with 20 mL of $C_2Cl_2$ and neutralized with 50% aq. NaOH (24 mL) to about pH 13. The mixture was extracted with total of 65 mL of $C_2Cl_2$, decolorized with 0.5 g of active carbon, filtered and concentrated to ca. 20 mL. Heptane (10 mL) was added to the hot $CH_2Cl_2$ solution and the solution was cooled to 0°–5° C. for 3 h. The white crystals were recovered by filtration and dried as cis-(1S,2R)-1-aminoindan-2-ol (2.45 g, 66% yield, 99.5% ee).

Alternatively, a mixture of the trans-benzamide from above (90g, 355 mmol) and 227 g of 80% wt $H_2SO_4$ was heated at 80°–85° C. for 1 h. The mixture was treated with 377 mL of water and heated to 100°–115° C. for 3.5 h. The mixture was cooled to 30°–35° C. and washed with 355 mL of $CH_2Cl_2$. The aqueous solution was then neutralized with 370 g of 50% NaOH at <50° C., and 175 mL water was added to dissolve the inorganic salts ($Na_2SO_4$). The aqueous mixture was extracted with 535 mL of $CH_2Cl_2$ at 30°–35° C., and the $CH_2Cl_2$ extracts decolorized with 4.5 g activated carbon and dried with 7.5 g $MgSO_4$ (anhydrous). The mixture was filtered through Celite and the filter cake washed with 100 mL of $CH_2Cl_2$. The combined filtrates were concentrated to ca. 450 mL and 215 mL heptane was added at 40° C. over 30 min. The solution was cooled to 0°–5° C. and the resulting solid recovered by filtration affording cis-(1S,2R)-1-aminoindan-2-ol (45.2 g, 84%>99.5% ee).

The corresponding cis (1R,2S)-1-aminoindan-2-ol may be obtained by the same procedure beginning with (S,S) salen.

The process stream from the aminolysis analogous to the procedure described above employing (S,S)-Salen was treated with 102 mL of HCl (36 wt. %) to pH<1.0 and extracted with 500 mL of methylene chloride. The aqueous phase was basified with 50% sodium hydroxide to pH=13 and extracted with 600 mL of methylene chloride at 30° to 35° C. The methylene chloride extracts were decolorized with 6.0 g of Darco G-60® and dried with 7.5 g of magnesium sulfate (anhydrous) at 30° to 35° C. The mixture was vacuum filtered and washed with 150 mL of methylene chloride. The filtrate was heated to reflux and 750 mL of heptane was added dropwise at 40° to 45° C. The slurry was cooled to 0° to 5° C. and held for three hours. The off-white product was collected by vacuum filtration and washed with 50 mL of heptane followed by drying in vacuo at 40° C., for 5 hours to afford 97.9 g (65.6% of theory, 94.7%ee) of (R,R)-trans-1-aminoindan-2-ol. Pure (S,S)-trans may be obtained in analogous fashion.

Use of Aminoindanols to Effect Resolution

The aminoindanols of the present invention can be used to separate the enantiomers of chiral acids including various drug products or intermediates leading to drug products, and they are relatively general in their applicability.

For example, using (1S,2R)-1-aminoindan-2-ol it is possible to separate the enantiomers of a range of commercially important chiral acids including ketoprofen, flurbiprofen, tetrahydrofuran carboxylic acid, cyclohexylphenyl glycolic acid and ibuprofen.

In a first series of experiments, diasteromeric salts of R- and S-ketoprofen with aminoindanol were shown to exhibit an unexpectedly large difference in solubility under a range of solvent conditions. (S)-Ketoprofen-(1S,2R)-aminoindanol and (R)-Ketoprofen-(1S,2R)-aminoindanol diasteromers (>99% diasteromeric excess) were utilized in the solubility studies.

TABLE 1

Solubilities of (R)- and (S)-ketoprofen diastereomer salts with (1S,2R)-1-aminoindan-2-ol in a range of solvents. Selectivity corresponds to the ratio of solubilities of the more soluble to the less soluble diastereomer.

| | Diastereomer Solubility (wt %) | | |
|---|---|---|---|
| Solvent | (R)-ketoprofen | (S)-ketoprofen | Selectivity |
| Tetrahydrofuran | 4.0 | 13.3 | 3.3 |
| Methyl isobutyl ketone | 3.5 | 17.0 | 4.8 |
| Isobutyl acetate | 0.3 | 13.0 | 43.3 |
| Isopropyl acetate | 0.2 | 13.0 | 65.0 |
| Ethyl acetate | 0.3 | 12.4 | 39.0 |
| Water | <0.02 | 1.5 | >75 |
| Acetonitrile[1] | 0.43 | 0.1 | 4.3 |

The results are from (1R,2S)-1-aminoindan-2-ol.

The results show that using (1S,2R)-aminoindanol allows unexpectedly selective crystallization of (R-)-ketoprofen in the presence of (S)-ketoprofen. Alternatively, using (1R,2S)-aminoindanol allows for the selective crystallization of (S)-ketoprofen in the presence of (R)-ketoprofen.

In the second set of experiments, diasteromeric salts of R- and S-ketoprofen with aminoindanol were shown to exhibit unexpectedly larger differences in solubilities than diastereomeric salts of R- and S-ketoprofen with other chiral amines.

TABLE 2

Solubilities of (R)- and (S)-ketoprofen diastereomer salts with various chiral amines in ethyl acetate. Selectivity corresponds to the ratio of the more soluble to the less soluble diastereomer.

| | Ketoprofen Diastereomer Solubility (wt %) | | |
|---|---|---|---|
| Chiral Amine | (R)-enantiomer | (S)-enantiomer | Selectivity |
| (1S,2R)-1-aminoindan-2-ol | 0.3 | 12.4 | 39.0 |
| Cinchonine | 0.8 | 0.2 | 4.0 |
| (R)-Phenylpropylamine | 1.9 | 7.4 | 3.9 |
| Cinchonidine | 1.1 | 0.3 | 3.7 |
| (R)-Methylbenzylamine | 1.3 | 1.3 | 1.0 |

In a third set of experiments, diastereomeric salts of R- and S-acids with aminoindanol were shown to exhibit an unexpectedly large difference in solubility for a range of chiral acids.

TABLE 3

Solubilities of diastereomer salts composed of chiral acids with (1S,2R)-1-aminoindan-2-ol. Selectivity corresponds to the ratio of the more soluble to the less soluble diastereomer.

| | | Diastereomer Solubility (wt %) | | |
|---|---|---|---|---|
| Solvent | Chiral Acid | (R)-enantiomer | (S)-enantiomer | Selectivity |
| methyl isobutyl ketone | ketoprofen | 3.5 | 17.0 | 4.8 |
| methanol | tartaric acid | 1.1 | 8.9 | 8.0 |

EXAMPLES

The invention is illustrated by the following examples.

(R)-Naproxen

A sample of 2.9 g (12.6 mmole) of (R,S)-naproxen was combined with 56.5 g of an acetonitrile/water mixture (3.8% water), heated to 40° C. and stirred until the mixture dissolved. The solution was treated with 0.78 g (5.2 mmole) of (1R,2S)-cis-1-aminoindan-2-ol, mixed for 10 minutes. Solids began to precipitate within seconds of adding the (1R,2S)-cis-1-aminoindan-2-ol. The solution was stirred for 15 minutes. The solids that formed were collected by filtration, and washed with acetonitrile. The acid was released by combining the wet solids with 50 mL of deionized water, 2 mL of 5N $H_2SO_4$, and 50 mL of tert-butyl methyl ether. After mixing, the aqueous phase was separated and the organic phase washed twice with 50 mL of deionized water. The organic phase was evaporated under vacuum. The weight of the solid residue was 1.3 g, and the specific optical rotation was $[\alpha_D]^{20°}$ $^C$=−31(C=1, MeOH).

(S)-Ketoprofen

A sample of 88.2 g (347 mmole) of (R,S)-ketoprofen was combined with 560 g of methyl isobutyl ketone, heated to 40° C. and stirred until the mixture dissolved. The solution was treated with 38.8 g (260 mmole) of (1R,2S)-cis-1-aminoindan-2-ol, mixed for 30 minutes, seeded with 1.4 g of (S)-ketoprofen (1R,2S)-cis-1-aminoindan-2-ol diastereomer salt and held at 40° C. for 1 hour. The mixture was cooled to 15° C. over the course of 4 hours and held at 15° C. for 47 hours. The solids that formed were collected by filtration, washed twice with 80 g of MIBK and dried under vacuum to yield 37.2 g of (S)-ketoprofen (1R,2S)-cis-1-aminoindan-2-ol diastereomer. A portion of the salt (about 50 mg) was treated with 10 drops of 5N $H_2SO_4$ to release the acid. The enantiomeric excess of the released acid was measured by chiral HPLC and found to be 95.8% (s)-Ketoprofen.

(S)-Ketoprofen

A sample of 100.7 g (396 mmole) of (R,S)-ketoprofen was combined with 565 g of an acetonitrile/water mixture (3.8% water), heated to 40° C. and stirred until the mixture dissolved. The solution was treated with 32.5 g (218 mmole) of (1R, 2S)-cis-1-aminoindan-2-ol, mixed for 10 minutes, and seeded with 1 mL of a slurry containing 7.5 mg of (S)-ketoprofen(1R,2S)-cis-1-aminoindan-2-ol diastereomer salt per mL of acetonitrile. The solution was held at 40° C. for 30 minutes and then cooled to 5° C. over the course of 4 hours and held at 5° C. for an additional 30 minutes. The solids that formed were collected by filtration, washed twice with 80 g of acetonitrile and dried under vacuum to yield 66.4 g of (S)-ketoprofen (1R,2S)-cis-1-aminoindan-2-ol diastereomer. A portion of the salt (about 50 mg) was treated with 10 drops of 5N $H_2SO_4$ to release the acid. The enantiomeric excess of the released acid was measured by chiral HPLC and found to be 97.2% (S)-Ketoprofen.

(R)-Ketoprofen

A sample of 126 g (500 mmol) of (R,S)-ketoprofen was combined with 800 g of methyl isobutyl ketone, heated to 40° C. and stirred until the mixture dissolved. The solution was treated with 74 g (500 mmol) of cis-(1S,2R)-1-aminoindan-2-ol, mixed for 30 minutes, seeded with 20 g of (R)-ketoprofen cis-(1S,2R)-1-aminoindan-2-ol diastereomer salt and held at 40° C. for 30 minutes. The mixture was cooled to 25° C. over the course of 4 hours and further cooled to 15° C. over the course of 1 hour and then held at 15° C. for 18 hours. The solids that formed were collected by filtration and dried under vacuum to yield 86 g of (R)-ketoprofen cis-(1S,2R)-1-aminoindan-2-ol diastereomer with an (R)-ketoprofen diastereomeric excess of 97%. The acid was released from the diastereomer salt by combining the solid with equal amounts (315 g) of ethyl acetate and aqueous (12 wt %) sulfuric acid. After mixing, the aqueous phase was separated (saved for recovery of aminoindanol) and the organic phase washed twice with equal volumes of water. The organic phase was evaporated under vacuum. The weight of the solid residue was 54 g (66% yield based on available enantiomer and corrected for added seed diastereomer salt crystals) corresponding to (R)-ketoprofen of 97% enantiomeric excess.

The two diastereomers, (S)-ketoprofen(1R,2S)-cis-1-aminoindan-2-ol and (R)-ketoprofen (1R,2S)-cis-1-aminoindan-2-ol, were prepared under identical conditions (using acetonitrile as a solvent). Loss on drying analysis showed a 2.5% weight loss for the (S)-ketoprofen(1R,2S)-cis-1-aminoindan-2-ol diastereomer and no weight loss for the (R)-ketoprofen(1R,2S)-cis-1-aminoindan-2-ol diastereomer. Infrared analysis of the two diastereomeric salts showed a distinct absorption band typical of acetonitrile in the (S)-ketoprofen(1R,2S)-cis-1-aminoindan-2-ol diastereomer only. NMR analysis of the two diastereomeric salts showed an absorption peak at 2 ppm (typical of acetonitrile) for the (S)-ketoprofen (1R,2S)-cis-1-aminoindan-2-ol diastereomer. The same peak was not observed for the (R)-ketoprofen(1R,2S)-cis-1-aminoindan-2-ol diastereomer. The two diastereomers were subjected to differential scanning calorimetry. The (S)-ketoprofen (1R,2S)-cis-1-aminoindan-2-ol diastereomer showed two unique endotherm peaks, the first one occurring at 93°–100° C. and the second one at 108°–115° C. The (R)-ketoprofen (1R,2S)-cis-1-aminoindan-2-ol diastereomer showed a single endotherm peak at 127°–132° C. The same two diastereomers, when prepared using toluene as a solvent, showed almost identical endotherm peaks at 127°–135° C. All of these findings strongly suggest that, when using acetonitrile as solvent, the (S)-ketoprofen(1R,2S)-cis-1-aminoindan-2-ol diastereomer precipitates as an acetonitrile solvate containing approximately ⅓–⅔ moles of acetonitrile per mole of diastereomer salt.

The addition of a small amount of water to the acetonitrile was found to have a significant impact on the rate of crystallization. When performing the precipitation at room temperature (20°–22° C.) and in the absence of water, precipitation of the diastereomer begins prior to all the (1R,2S)-cis-1-aminoindan-2-ol being dissolved. As the amount of water in acetonitrile was increased to 3.8% it was found that all the (1R,2S)-cis-1-aminoindan-2-ol could be dissolved resulting in a clear solution. Other experiments done at 40° C. with various concentrations of water showed a definite trend; as the amount of water is increased, the start of the crystallization takes longer and the rate of crystallization is slower.

Racemization of (R)-Ketoprofen

To 468 g of a toluene/(R)-ketoprofen (63% EE) solution containing 94 g of ketoprofen, 671 g of deionized water was added followed by 153 g of 50% NaOH. The phases were mixed and then separated. The aqueous phase was heated to 115° C. (under pressure) and maintained at this temperature for 3 hours. The solution was then cooled to room temperature and 842 g of toluene were added, followed by 103 g of concentrated sulfuric acid. The phases were mixed and the aqueous phase decanted. After decolorization with activated carbon, the organic phase was concentrated to 25% ketoprofen concentration. The concentrate was cooled to 0° C. and kept at this temperature for 5 hours. The solids were filtered, washed with toluene, and dried under vacuum. The weight of the racemized ketoprofen was 62 g and the enantiomeric excess was 1.4% (R)-ketoprofen.

Resolution of Ketoprofen with cis-(1R,2S)-1-aminoindan-2-ol and triethylamine and racemization of unwanted (R)-Ketoprofen A sample of 100.7 g (396 mmole) of (R,S)-ketoprofen was combined with 565 g of an acetonitrile/water mixture (3.8% water), heated to 40° C. and stirred until the mixture dissolved. While mixing, 18 g (178 mmoles) of triethylamine were added. The solution was then treated with 32.4 g (217 mmole) of (1R,2S)-cis-1-aminoindan-2-ol, mixed for 10 minutes, and seeded with 1 mL of a slurry containing 7.5 mg of (S)-ketoprofen (1R,2S)-cis-1-aminoindan-2-ol diastereomer salt per mL of acetonitrile. The solution was held at 40° C. for 30 minutes and then cooled to 5° C. over the course of 4 hours and held at 5° C. for an additional 30 minutes. The solids that formed were collected by filtration, washed twice with 80 g of acetonitrile and dried under vacuum to yield 63.9 g of (S)-ketoprofen (1R,2S)-cis-1-aminoindan-2-ol diastereomer. A portion of the salt (about 50 mg) was treated with 10 drops of 5N $H_2SO_4$ to release the acid. The enantiomeric excess of the released acid was measured by chiral HPLC and found to be 96.2% (S)-ketoprofen.

The enantiomeric excess of the ketoprofen in the collected filtrate was measured by chiral HPLC and found to be 62.6% (R)-ketoprofen. The filtrate was evaporated under vacuum to a weight of 86.3 g. Subsequently, 100 g of acetonitrile and 87.7 g (867 mmoles) of triethylamine were added to the concentrate. The (R)-ketoprofen was racemized by heating the solution to 120° C. (under pressure) for two hours. The enantiomeric excess of the ketoprofen in the racemized solution was measured by chiral HPLC and found to be 10.3% (R)-ketoprofen.

(S)-Flurbiprofen

A sample of 6.2 g (25 mmol) of R,S flurbiprofen was combined with 40 g of methanol and stirred until dissolved. The solution was treated with 3.14 g (21 mmol) of cis-(1R,2S)-1-aminoindan-2-ol, seeded with a small amount of (1R,2S)-1-aminoindan-2-ol (S)-flurbiprofen diastereomer, and allowed to crystallize over a period of 17 hours at ambient temperature. The mixture was then cooled and held at 4° C. for 5 hours. The solids were isolated by filtration, washed with 35 mL methanol, and dried to afford 3.8 g (38M % yield) of white crystals. The acid was released by dissolving the solid in 200 mL of an ethyl acetate-water (50/50; v/v) mixture and treating the solution with 3 g of 5N aqueous sulfuric acid. After mixing, the aqueous phase was decanted and the organic phase washed twice with 100 mL of water. The organic phase was then evaporated under vacuum. The weight of the solid residue was 2.1 g. The rotation $[\alpha]_D$ of this solid was −18.8 (c=1, ethanol) corresponding to (S)-flurbiprofen of 44.6% enantiomeric excess.

(S)-Tetrahydrofuran carboxylic acid

A mixture of 1.16 g of racemic tetrahydro-2-furoic acid (97 wt % chemical purity, 10 mmol) in 9 g of 4-methyl-2-pentanone was heated at 40°–50° C. for 10 minutes. The solution was treated with 0.66 g of (1S,2R)-cis-1-aminoindan-2-ol (4.4 mmol, >99.5% ee, 99 wt % chemical purity) and maintained at 40°–45° C. for 15 minutes. The mixture was slowly cooled to 5°–10° C. and the resulting white solid recovered by filtration, affording 0.75 g of (1S,2R)-1-aminoindan-2-ol tetrahydro-2-furoic acid diastereomer [64M % yield, mp=150°–152° C., $[\alpha]_D$=−31° (C=0.606, methanol)]. The acid was released by treating the solid with a mixture of dichloromethane and 5N aqueous sulfuric acid. After mixing, the aqueous phase was removed and the organic phase washed with water. The organic phase was evaporated to yield solid (S)-(-)-tetrahydrofuran carboxylic acid.

(R)-Cyclohexylphenyl Glycolic Acid

A mixture consisting of 1.17 g (5 mmol) of racemic cyclohexylphenyl glycolic acid (98 wt % chemical purity), 0.75 g (5 mmol) of cis-(1S,2R)-1-aminoindan-2-ol in 23 mL of an ethyl acetate-ethanol mixture (20/3; v/v) was heated at reflux until all solids dissolved. The resulting solution was then allowed to cool to ambient temperature and held until solids formed. The solids were collected by filtration affording 0.23 g of cis-(1S,2R)-1-aminoindan-2-ol (R)-cyclohexylphenyl glycolic acid (12M %). HPLC analysis showed the presence of 98.6% diastereomeric excess of (R)-cyclohexylphenyl glycolic acid. The acid was released by treating the mixture with equal volumes (50 mL) of ethyl acetate and aqueous hydrochloric acid (5 wt %). After mixing, the aqueous phase was removed and the organic phase was washed with an equal volume of water. The organic phase was evaporated under vacuum to yield solid (R)-cyclohexylphenyl glycolic acid of 98.6% enantiomeric excess.

Recovery of Aminoindanol

This example illustrates that aminoindanol can be recovered for reuse, an important feature for commercial applications. Aqueous phase containing cis-(1S,2R)-1-aminoindan-2-ol sulfate was evaporated until the concentration of aminoindanol was 20 g per 100 g of water. The acidic aqueous aminoindanol concentrate was treated with aqueous sodium hydroxide (50 wt %) with cooling and vigorous stirring until the pH was raised above 10. The resulting slurry of aminoindanol was mixed at 20° C. for 1 hour. The solids were isolated by filtration and washed with cold (9° C.) water to yield cis-(1S,2R)-1-aminoindan-2-ol with 84% recovery.

As will be apparent from the examples above, the particular acid used to liberate the chiral acid from the diastereomeric salt is not critical. Indeed the chiral acid could be recovered as its salt using a strong base. Normally, a mineral acid would be used; any acid that is a stronger acid than the chiral acid and that exhibits high water solubility would be suitable; other acids could be used, but would not be preferred.

The aminoindanol may be added to the solution of chiral acid enantiomers either undiluted or as a solution in a suitable solvent. The indanol may be used in any proportion desired, but the use of much more than one equivalent is wasteful and we have observed no advantage to such proportions. The optimal ratio for separating a racemic mixture of chiral acid by crystallization appears to be 0.4 to 0.6 equivalents (i.e. about the amount needed to form the less soluble diasteromeric salt). In some cases it may be advantageous to use less than one equivalent of aminoindanol and replace the remainder with another base; this often provides advantages in cost, solubility or ease of recycling the residual enantiomer through a racemization process such as the one described above for R-ketoprofen. It may also be advantageous, for the same reasons, in some cases to begin with a salt derived from the carboxylic acid and an achiral base (e.g. a sodium, potassium or ammonium salt) rather than with the free acid.

We claim:

1. A process for the resolution of an enantiomer mixture of a chiral acid of formula $R^1R^2R^3CCOOH$ or a salt thereof wherein
$R^1$ is hydrogen or OH;
$R^2$ is methyl or cyclohexyl; and
$R^3$ is aryl, substituted aryl or heteroaryl;
or $R^2$ and $R^3$ together form a tetrahydrofuran or tetrahydropyran ring;
said process comprising the steps of;
(a) preparing a mixture of said acid or salt thereof with an enantiomer of 1-aminoindan-2-ol in a suitable solvent;
(b) separating said mixture into a first fraction enriched in one enantiomer of said acid as a diastereomeric salt and a second fraction enriched in a second enantiomer; and
(c) recovering said chiral acid from at least one of said fractions.

2. A process according to claim 1 wherein said separating said mixture is accomplished by fractional crystallization.

3. A process for resolving a mixture of enantiomers of chiral carboxylic acid of formula $R^1R^2R^3CCOOH$ or salt thereof wherein $R^1$ is hydrogen or OH;

$R^2$ is methyl or cyclohexyl; and $R^3$ is aryl, substituted aryl or heteroaryl;

or $R^2$ and $R^3$ together form a tetrahydrofuran or tetrahydropyran ring;

comprising the steps of:

(a) dissolving a mixture of enantiomers of said chiral carboxylic acid or salt thereof in a suitable solvent;

(b) adding a substantially pure enantiomer of a 1-aminoindan-2-ol to create a diastereomeric salt of at least one enantiomer;

(c) allowing said diastereomeric salt to crystallize to form a solid phase, whereby a salt comprising said 1-aminoindan-2-ol and a first enantiomer of said chiral acid predominates in said solid phase and a second enantiomer of said chiral acid predominates in the solution phase;

(d) recovering said solid phase from said solution phase; and (e) recovering said chiral acid from at least one of said phases.

4. A process according to either of claims 1 or 3 wherein said enantiomer of a 1-aminoindan-2-ol is present in an amount of from 0.1 to 1.1 equivalents based on said carboxylic acid.

5. A process according to either of claims 1 or 3 wherein said enantiomer of a 1-aminoindan-2-ol is present in an amount of from 0.4 to 0.6 equivalents based on said carboxylic acid.

6. A process according to either of claims 1 or 3 wherein said 1-aminoindan-2-ol is (1R,2S)-1-aminoindan-2-ol.

7. A process according to either of claims 1 or 3 wherein said 1-aminoindan-2-ol is (1R,2R)-1-aminoindan-2-ol.

8. A process according to either of claims 1 or 3 wherein said 1-aminoindan-2-ol is (1S,2R)-1-aminoindan-2-ol.

9. A process according to either of claims 1 or 3 wherein said 1-aminoindan-2-ol is (1S,2S)-1-aminoindan-2-ol.

10. A process according to either of claims 1 or 3 wherein, in said chiral acid, $R^1$ is hydrogen.

11. A process according to claim 10 wherein $R^2$ is methyl.

12. A process according to claim 11 wherein said chiral acid is chosen from the group consisting of ketoprofen, ibuprofen, flurbiprofen, and naproxen.

13. A process according to claim 12 wherein said chiral acid is ketoprofen.

14. A process according to claim 12 wherein said solvent is at least in part acetonitrile.

15. A process according to either of claims 1 or 3 wherein, in said chiral acid, $R^1$ is hydroxyl and $R^2$ is cyclohexyl.

16. A process according to either of claims 1 or 3 wherein said chiral acid is tetrahydrofuran-2-carboxylic acid.

17. A process according to either of claims 1 or 3 further including the steps of recovering a non-racemic mixture of the enantiomers of said carboxylic acid, said mixture being enriched in said second enantiomer, racemizing the mixture and recycling the racemized mixture.

18. A salt of an optically active 1-aminoindan-2-ol and a chiral carboxylic acid of formula $$R^1R^2R^3CCOOH$$

wherein $R^1$ is hydrogen or OH;

$R^2$ is methyl or cyclohexyl; and $R^3$ is aryl, substituted aryl or heteroaryl;

or $R^2$ and $R^3$ together form a tetrahydrofuran or tetrahydropyran ring.

19. A salt according to claim 18 wherein $R^1$ is hydrogen and $R^2$ is methyl.

20. A salt according to claim 19 wherein said carboxylic acid is chosen from the group consisting of ketoprofen, ibuprofen, flurbiprofen, and naproxen.

21. A salt according to claim 20 wherein said carboxylic acid is ketoprofen.

22. A salt according to claim 21 which is a solvate with acetonitrile.

23. A salt according to claim 18 wherein $R^1$ is hydroxyl and $R^2$ is cyclohexyl.

24. A salt according to claim 18 wherein said chiral acid is tetrahydrofuran-2-carboxylic acid.

* * * * *